US012746165B2

(12) United States Patent
Jäger et al.

(10) Patent No.: US 12,746,165 B2
(45) Date of Patent: Sep. 29, 2026

(54) REMOTE CONTROL NEARFIELD DETECTION

(71) Applicant: Baxter Medical Systems GmbH + Co. KG, Saalfeld (DE)

(72) Inventors: Matthias Jäger, Rudolstadt (DE); Leonard Zeh, Saalfeld (DE)

(73) Assignee: Baxter Medical Systems GmbH & Co. KG (DE)

( * ) Notice: Subject to any disclaimer, the term of this patent is extended or adjusted under 35 U.S.C. 154(b) by 73 days.

(21) Appl. No.: 18/747,529

(22) Filed: Jun. 19, 2024

(65) Prior Publication Data

US 2025/0000734 A1 Jan. 2, 2025

Related U.S. Application Data

(60) Provisional application No. 63/511,321, filed on Jun. 30, 2023.

(51) Int. Cl.

*G16H 40/40* (2018.01)
*A61G 13/10* (2006.01)
*G16H 40/67* (2018.01)

(52) U.S. Cl.

CPC ........... *A61G 13/104* (2013.01); *G16H 40/40* (2018.01); *G16H 40/67* (2018.01)

(58) Field of Classification Search

CPC ...... A61G 13/104; A61G 13/02; G16H 40/40; G16H 40/67

USPC .............................................................. 5/600

See application file for complete search history.

(56) References Cited

U.S. PATENT DOCUMENTS

| | | | | |
|---|---|---|---|---|
| 7,010,369 | B2 | 3/2006 | Borders et al. | |
| 9,230,421 | B2 | 1/2016 | Reeder et al. | |
| 9,661,119 | B2 | 5/2017 | Mankopf et al. | |
| 10,019,612 | B2 | 7/2018 | Theurer et al. | |
| 10,515,189 | B2 * | 12/2019 | Ting ....................... | G16H 20/13 |
| 10,835,348 | B2 | 11/2020 | Poirier et al. | |
| 10,945,905 | B2 | 3/2021 | Hoel et al. | |
| 2009/0231179 | A1 * | 9/2009 | Bruhn .................... | G08C 17/02 341/176 |

(Continued)

OTHER PUBLICATIONS

TruSystem 7500 Operating Table Column Instruction Manual (Nov. 2, 2017).

TruSystem 7000 Operating Table Instruction Manual (Nov. 2016).

*Primary Examiner* — David R Hare
*Assistant Examiner* — Joseane E. Tejada
(74) *Attorney, Agent, or Firm* — Price Heneveld LLP

(57) ABSTRACT

A patient support apparatus is provided that includes: a removable table; a support structure comprising a support column having an adjustable height, the support column having a column head at an upper end thereof for receiving and supporting the removable table; an actuator for adjusting the height of the support column; a wireless receiver for receiving control signals from a remote control; an RF reader positioned proximate the column head for receiving RF signals from an RFID tag on the remote control; and a controller coupled to the actuator, and to the RF reader for controlling the actuator in response to control signals from the remote control. The controller is configured to detect whether the remote control is within a predetermined distance from the column head and to disable upward movement of the support column when the presence of the remote control is detected within the predetermined distance.

40 Claims, 9 Drawing Sheets

(56) References Cited

U.S. PATENT DOCUMENTS

| | | | | |
|---|---|---|---|---|
| 2013/0239330 | A1 | 9/2013 | Newlin | |
| 2014/0159912 | A1* | 6/2014 | Fraden | G16H 40/67 340/870.02 |
| 2015/0366521 | A1 | 12/2015 | Truta | |
| 2021/0052450 | A1 | 2/2021 | Ojha | |
| 2021/0196549 | A1* | 7/2021 | Hoel | A61G 13/104 |

* cited by examiner

REMOTE CONTROL NEARFIELD DETECTION

CROSS-REFERENCE TO RELATED APPLICATION

This application claims priority under 35 U.S.C. § 119(e) upon U.S. Provisional Patent Application No. 63/511,321, entitled "REMOTE CONTROL NEARFIELD DETECTION" filed on Jun. 30, 2023, by Matthias Jager et al., the entire disclosure of which is incorporated herein by reference.

FIELD OF THE DISCLOSURE

The present disclosure generally relates to a system and method for nearfield detection of a remote control, and more particularly to a system and method for nearfield detection of a remote control used to control a patient support apparatus such as an operating table.

SUMMARY OF THE DISCLOSURE

According to one aspect of the present disclosure, a support structure is provided for supporting a removable table of a patient support apparatus, the support structure comprising: a support column having an adjustable height, the support column including a column head at an upper end of the support column for receiving and supporting the removable table; an actuator for adjusting the height of the support column; a wireless receiver for receiving control signals from a remote control; an RF reader positioned proximate the column head for receiving RF signals from an RFID tag on the remote control; a user interface positioned on the support column for providing control signals; and a controller coupled to the user interface, the actuator, the wireless receiver, and to the RF reader for controlling the actuator in response to control signals, wherein the controller is configured to detect whether the remote control is within a predetermined distance from the column head and to disable upward movement of the support column when the remote control is detected within the predetermined distance.

According to another aspect of the present disclosure, a patient support apparatus is provided comprising: a removable table; a support structure comprising a support column having an adjustable height, the support column having a column head at an upper end thereof for receiving and supporting the removable table; an actuator for adjusting the height of the support column; a remote control; a wireless receiver for receiving control signals from the remote control; an RF reader for receiving RF signals from an RFID tag, wherein one of the RF reader and the RFID tag is on the remote control and the other of the RF reader and the RFID tag is positioned proximate the column head; and a controller coupled to the actuator and the wireless receiver, the controller being in communication with the RF reader for controlling the actuator in response to control signals from the remote control, wherein the controller is configured to detect whether the remote control is within a predetermined distance from the column head and to disable upward movement of the support column when the presence of the remote control is detected within the predetermined distance.

According to another aspect of the present disclosure, a patient support apparatus is provided comprising: a support structure comprising: a chassis having a plurality of wheels for allowing movement of the patient support apparatus; a motor for rotating at least one of the plurality of wheels to propel the patient support apparatus in at least one direction; and a support column supported on the chassis; a table supported by the support column; a remote control; a wireless receiver for receiving control signals from the remote control; an RF reader for receiving RF signals from an RFID tag, wherein one of the RF reader and the RFID tag is on the remote control and the other of the RF reader and the RFID tag is associated with the support structure; and a controller coupled to the motor and the wireless receiver, the controller being in communication with the RF reader for controlling a plurality of functions of the patient support apparatus in response to control signals from the remote control, wherein one of the functions is the actuation of the motor, wherein the controller is configured to detect whether the remote control is within a predetermined distance from the table and wherein the controller is further configured to disable actuation of the motor in response to control signals received from the remote control when the remote control is not detected within the predetermined distance, wherein the controller controls the other functions of the patient support apparatus in response to control signals from the remote control regardless of the detection of the remote control within the predetermined distance.

According to another aspect of the present disclosure, a method is provided for controlling a transfer of a removable operating table from a shuttle to a support structure having a support column having an adjustable height, the support column having a column head at an upper end thereof for receiving and supporting the removable table, the method comprising the steps of: detecting whether a remote control is within a predetermined distance from the column head; disabling upward movement of the support column when the remote control is detected within the predetermined distance; and allowing upward movement of the support column when the remote control is not detected within the predetermined distance, wherein such upward movement of the support column lifts the operating table upward off the shuttle to transfer the operating table from the shuttle to the support structure.

These and other features, advantages, and objects of the present disclosure will be further understood and appreciated by those skilled in the art by reference to the following specification, claims, and appended drawings.

DETAILED DESCRIPTION

Figure 1:
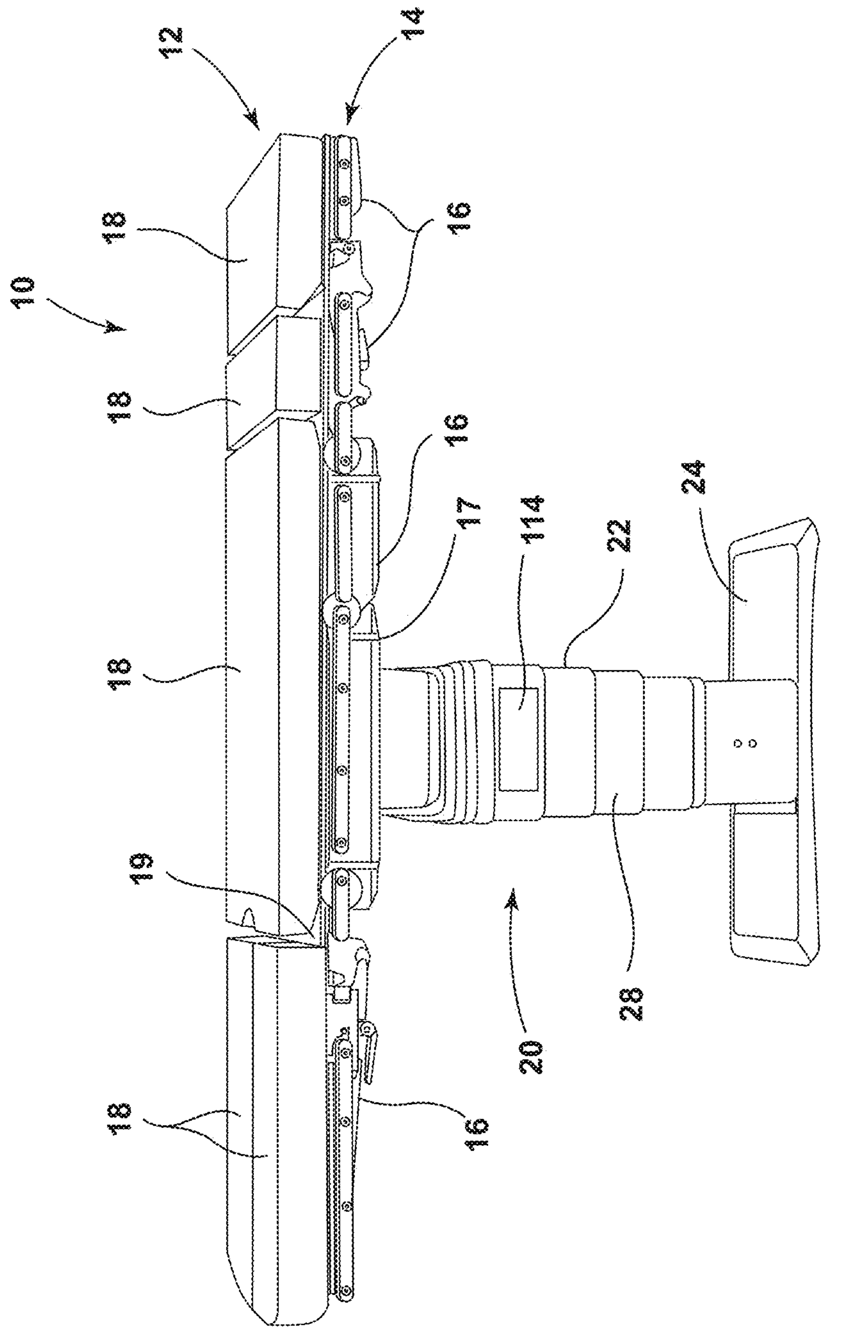
FIG. 1 is an elevational perspective side view of a patient support apparatus according to a first embodiment.

The present illustrated embodiments reside primarily in combinations of method steps and apparatus components related to a patient support apparatus. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms “upper,” “lower,” “right,” “left,” “rear,” “front,” “vertical,” “horizontal,” and derivatives thereof, shall relate to the disclosure as oriented in FIG. 1. Unless stated otherwise, the term “front” shall refer to a surface closest to an intended viewer, and the term “rear” shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms “including,” “comprises,” “comprising,” or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by “comprises a . . . ” does not, without more constraints, preclude the existence of additional identical elements in the process, method, article, or apparatus that comprises the element.

As noted above, the embodiments described below relate to a system and method for nearfield detection of a remote control used to control a patient support apparatus such as an operating table. To provide context, some details of patient support apparatus will first be described.

Figure 2:
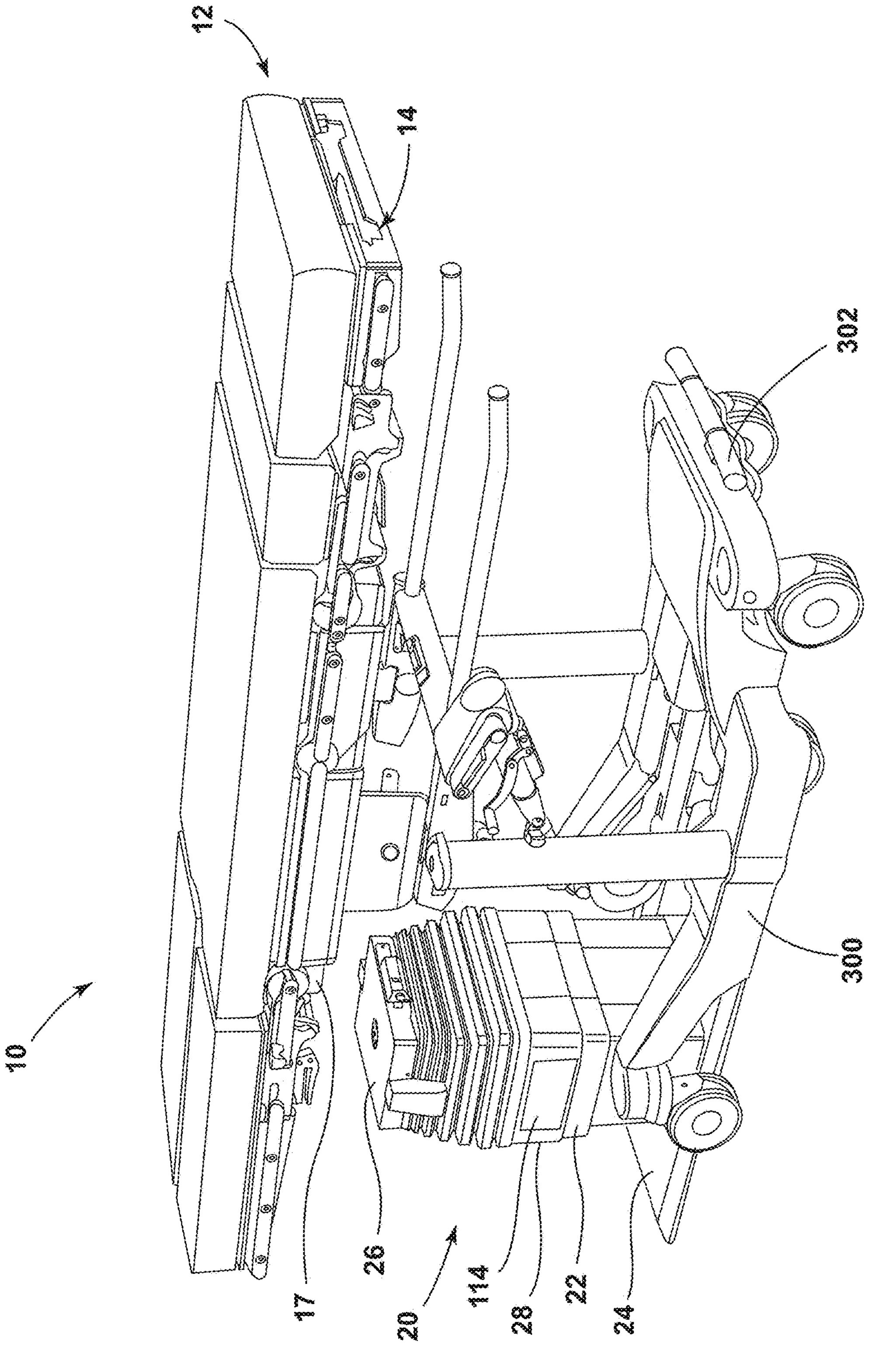
FIG. 2 is an elevational perspective side view of the patient support apparatus shown in FIG. 1 with a shuttle transferring a table to a support structure.
Figure 3:
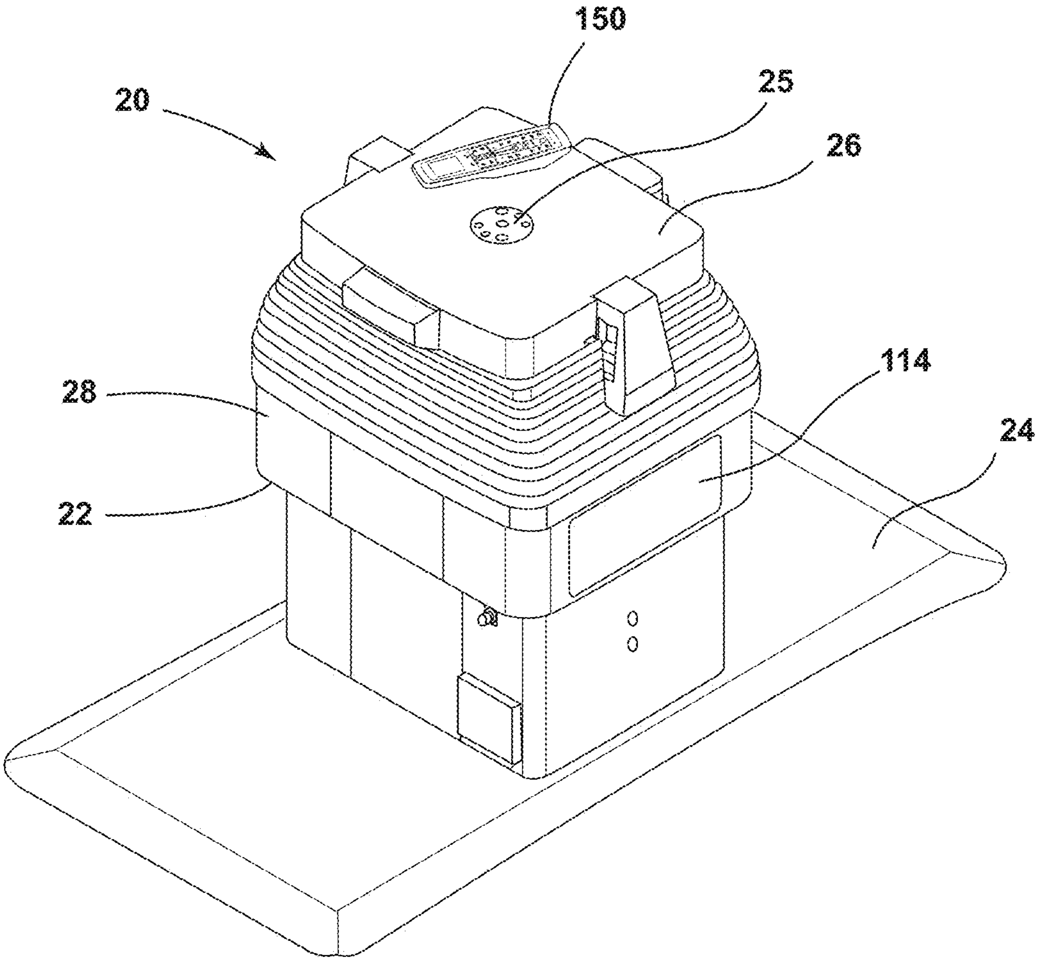
FIG. 3 is an elevational perspective side view of the support structure of the patient support apparatus shown in FIGS. 1 and 2.

Referring to FIGS. 1-3, reference numeral 10 generally designates a patient support apparatus that has a table 12 and a support structure 20 that supports the table 12. A controller 102 (FIG. 4) is operably coupled to the patient support apparatus 10 for controlling various functions of the support structure 20 and table 12 as described further below.

Referring to FIG. 1, the patient support apparatus 10 is illustrated as a surgical table within a healthcare setting, such as a surgical suite. The table 12 includes a support frame 14 for supporting the patient thereon. One or more pads 18 may be selectively disposed on a top support surface 19 of the support frame 14. As illustrated in FIG. 1, multiple pads 18 are arranged along the top support surface 19 of the support frame 14. The pads 18 may be disposed in a spaced-apart arrangement along the top support surface 19, or alternatively, may be directly coupled to one another. Alternatively, the support frame 14 may include a single pad 18 covering at least a portion of the top support surface 19.

The support frame 14 generally includes a plurality of segments 16 that are each pivotally coupled to one or two adjacent segments 16. The segments 16 are independently movable relative to one another. In this way, a single segment 16 may be rotated to an incline, rotated to a decline, or otherwise moved relative to the remaining stationary segments 16. The independently movable segments 16 may be advantageous for aligning the patient on the support frame 14 for one or more surgical procedures or other treatment of the patient.

According to various aspects, the patient support apparatus 10 includes the support structure 20 coupled to a bottom surface 17 of the support frame 14. In the embodiment shown in FIGS. 1-3, the support structure 20 includes a base plate 24 and a support column 22 extending upward from the base plate 24. The base plate 24 may be fixed to the floor of the operating room or may not be fixed so as to be movable within the operating room.

As best shown in FIG. 3, the support column 22 may have a column head 26 at its upper end for engaging the bottom surface 17 of the support frame 14. In the embodiment shown in FIGS. 1-3, the table 12 is removable. FIG. 1 shows the removable table 12 fully supported on the support structure 20. FIG. 2 shows the removable table 12 removed from the support structure 20 using a shuttle 300. FIG. 3 shows the support structure 20 with the table 12 removed.

The patient support apparatus 10 generally includes an adjustment system 110 (FIG. 4) that includes various electromechanical actuators 112 in both the table 12 and the support column 22 that are selectively operated under the control of the controller 102, which may be located in the support column 22. Actuators 112 in the table 12 adjust the positioning of the movable segments 16. A connection terminal 25 (FIG. 3) is provided on the column head 26 to provide electrical connection of the controller 102 to the actuators 112 in the table 12. Actuators 112 in the table 12 adjust the positioning of the movable segments 16. Actuators 112 in the support column 22 may adjust the height and inclination angles of the table 12 and may be provided in a protective shroud 28. Accordingly, the protective shroud 28 is flexible and may have grooves or folds based on the position of the table 12.

Figure 4:
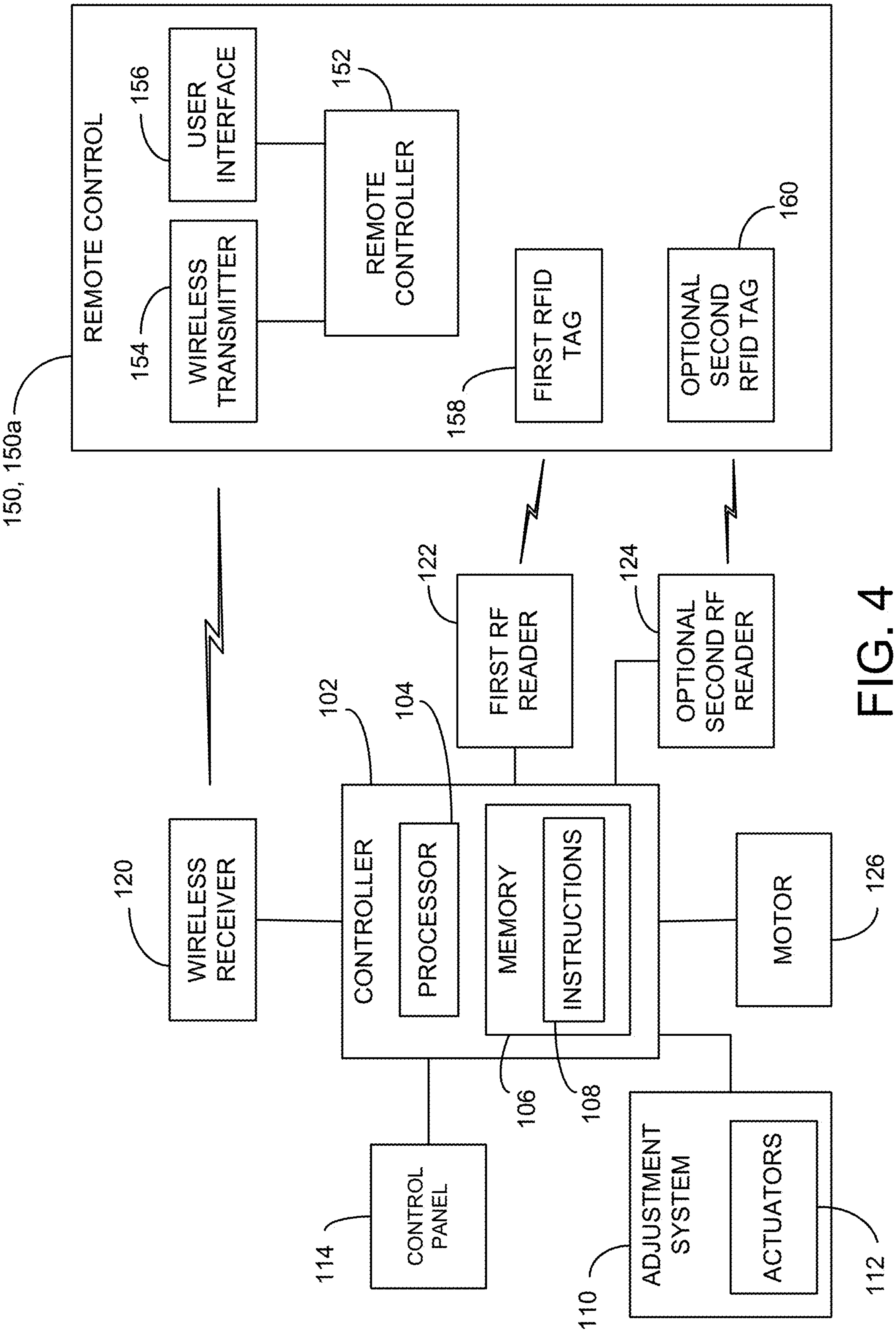
FIG. 4 is an electrical circuit diagram in block form of a remote control and components used in the patient support apparatus of FIGS. 1-3 and 7.

Referring to FIG. 4, the controller 102 may include a processor 104, a memory 106, and other control circuitry. The controller 102 includes routines or instructions 108 stored within the memory 106 and executable by the processor 104. The controller 102 controls the actuators 112 of the adjustment system 110 in response to control signals received from a control panel 114 that may be located on one side of the support column 22. The controller 102 may also receive control signals from a wireless transmitter 154 of a remote control 150 via a wireless receiver 120 that is coupled to the controller 102. FIG. 4 shows the basic electrical components of the remote control 150 and FIG. 5 shows an example of such a remote control 150.

Figure 5:
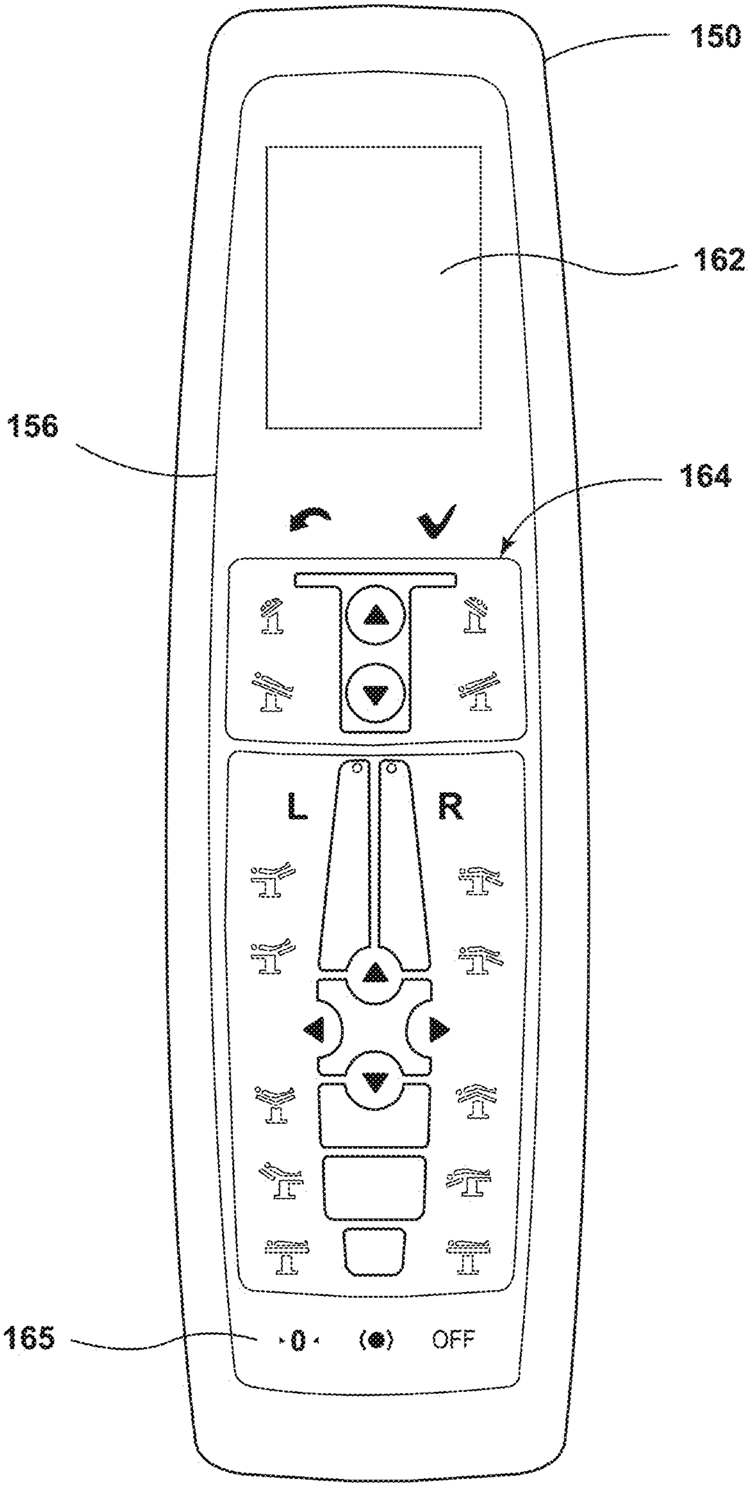
FIG. 5 is a top plan view of a remote control that is used with the patient support apparatus shown in FIGS. 1-3.

As shown in FIGS. 4 and 5, the remote control 150 may include a remote controller 152, which may include a processor or the like, and a user interface 156, which may be a touch screen display 162 and/or include input buttons 164 (FIG. 5). The remote controller 152 may respond to inputs received from the user interface 156 by sending control signals to wireless transmitter 154, which then wirelessly transmits the control signals to the wireless receiver 120 of the support column 22. The remote control 150 further includes a first RFID tag 158 having a unique serial number.

One of the input buttons 164 may be a transfer button 165. When pressed, the transfer button 165 causes the remote control 150 to send a transfer signal to the controller 102 via wireless transmitter 154 and wireless receiver 120. The controller 102 responds to a transfer signal by energizing the actuator 112 that raises and lowers the column head 26. If the column head 26 is in a raised position, the controller 102 will cause the actuator 112 to lower the column head 26 so that the shuttle 300 carrying a table 12 may be moved above the column head 26. Once the column head 26 is lowered or if it is already in a lowered position, the shuttle 300 moves the table 12 into position and the controller 102 then raises the column head 26 until it engages the bottom surface 17 of the support frame 14 of the table 12 and lifts the table 12 from the shuttle 300. The shuttle 300 then is moved out from beneath the table 12 so that the table 12 may be adjusted to a desired height. The shuttle 300 may be motorized and operated using either remote control 150, its own remote control, or control features physically mounted on the shuttle 300.

The transfer signal received by the wireless receiver 120 may come from the remote control 150 or from the shuttle 300 itself when a transfer foot pedal 302 is pressed. When a table 12 is supported by the support structure 20, a command may be issued by either the remote control 150 or the shuttle 300 to cause the table 12 to be lifted to a height that allows the shuttle to be moved under the table 12 and then to lower the table 12 onto the shuttle 300 for transport of a patient following surgery. Such a transfer function and shuttle are known in the art and part of the TruSystem™ 7500 and the compatible power shuttle available from Trumpf Medical or the TS7500 and the compatible power shuttle available from Hill-Rom. Additional details of the operation of the TruSystem™ 7500/TS7500 and the shuttle may be found in their respective operating manuals.

Referring back to FIG. 3, one problem with a patient support apparatus 10 having a removable table 12 is that the remote control 150 may inadvertently be placed on top of the column head 26 when the table 12 is removed. This may be a problem when a table 12 is brought into the operating room to be transferred onto the column head 26 since the table 12 may first be rolled into position over the top of the column head 26 and the remote control 150. Then an input may be provided on the control panel 114 to perform a transfer function whereby an actuator 112 moves the column head 26 upward to engage the bottom surface 17 of the support frame 14. However, if the remote control 150 is located on top of the column head 26, it may get damaged or may prevent the column head 26 from properly engaging the bottom surface 17 of the support frame 14. In the latter case, the table 12 may not be properly secured to the support column 22 and the table 12 could fall off resulting in potential injury to the patient.

To solve this problem, a detection means is provided for detecting when the remote control 150 is located proximate the column head 26 as well as a transfer prevention means for preventing the transfer function to be performed whereby the column head 26 is raised, when the detection means detects the proximity of the remote control 150.

The detection means may include the combination of the first RFID tag 158 and a first RF reader 122, wherein one of the RFID tag 158 and the first RF reader 122 is positioned on the remote control 150 and the other one of the RFID tag 158 and the RF reader 122 is positioned proximate the column head 26 for sending and receiving RF signals to/from the first RFID tag 158. If a passive RFID tag 158 is used, the first RFID tag 158 responds to signals sent from the first RF reader 122 by sending a return signal with its unique serial number back to the first RF reader 122. The first RF reader 122 only receives a return signal from the first RFID tag 158 when the first RFID tag 158 is within a predetermined distance from the first RF reader 122. For example, the predetermined distance may be about 30 cm. Although the RFID tag 158 is described above as a passive RFID tag, it may instead be an active RFID tag such that the RF reader 122 does not have to first send a signal to the RFID tag, but rather receives signals periodically sent from the RFID tag. In this case the RFID tag 158 would be powered by the remote control 150 rather than the signal sent from the RF reader 122. In addition, rather than having the RFID tag 158 associated with the remote control, the RFID tag 158 instead may be associated with the support structure 20 and located proximate the column head 26 while the RF reader 122 may be associated with the remote control 150. In this case, if the RFID tag 158 is not in range of the remote control 150, the remote control may send a signal to the controller 102 via the wireless receiver 120. Further, although the detection means is described above as including an RF reader and an RFID tag on the remote control, various forms of proximity or nearfield sensors could also be used.

The transfer prevention means may be embodied by a software routine 400 (FIG. 6) executed by the controller 102 whereby the controller 102 responds to the receipt of a return signal by the first RF reader 122 by blocking the performance of a transfer function that would otherwise cause the column head 26 to rise to engage the bottom surface 17 of the support frame 14. In other words, the controller 102, which controls actuation of the actuator 112 that raises the support column 22 in response to control signals, is configured to detect the presence of the remote control 150 within a predetermined distance from the column head 26 and to disable upward movement of the support column 22 when the presence of the remote control 150 is detected.

Figure 6:
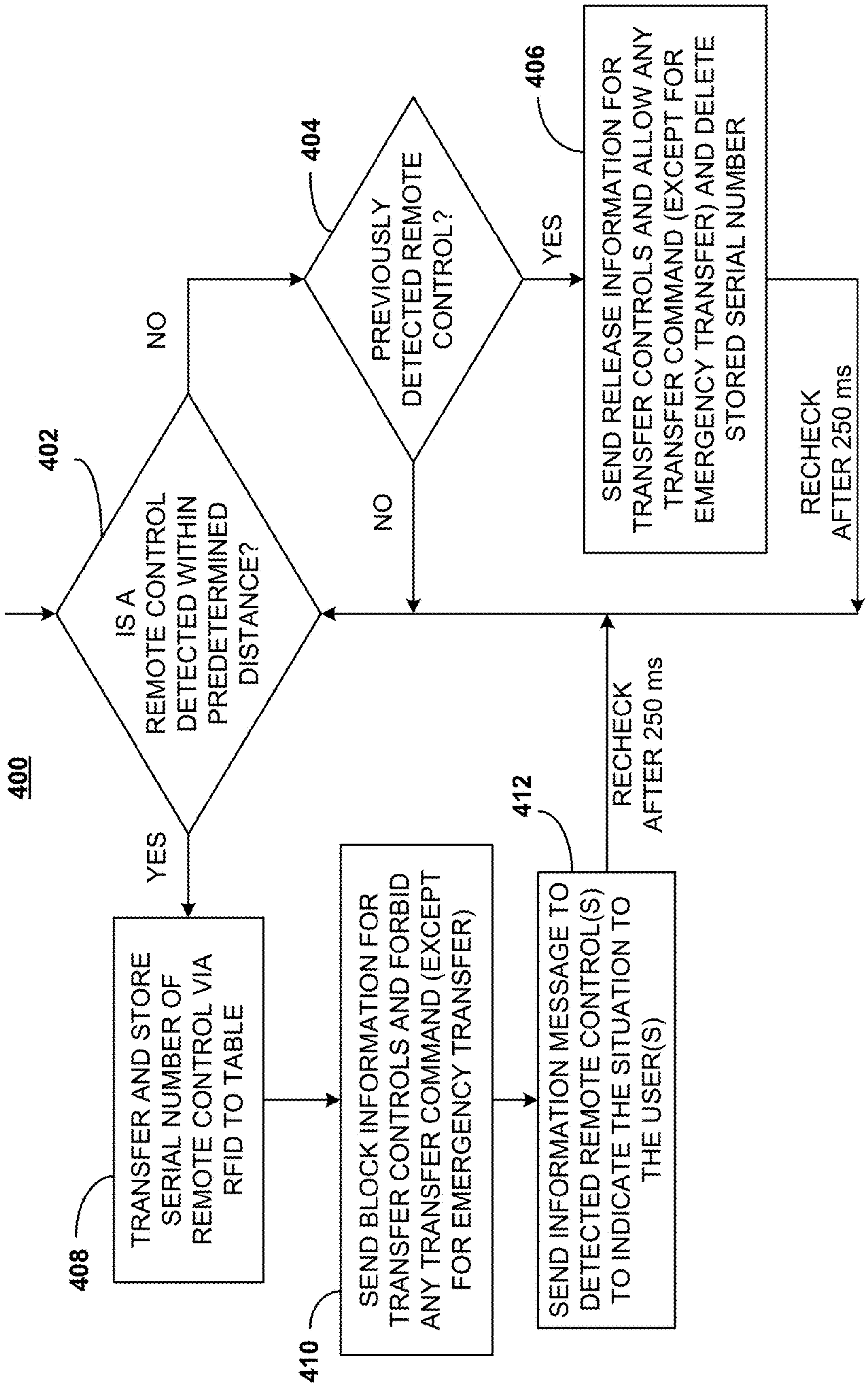
FIG. 6 is a flow chart showing a routine executed by a controller shown in FIG. 4 when used for the patient support apparatus shown in FIGS. 1-3.

FIG. 6 is a flowchart illustrating a routine 400 executed by the controller 102 to perform the above blocking/unblocking of the transfer function. The routine 400 begins with a determination of whether a remote control 150 is detected within the predetermined distance (e.g., approximately 30 cm) of the column head 26 (step 402). If a remote control 150 is not detected within the predetermined distance, the controller 102 then determines if there was a previously detected remote control 150 by checking a table in which serial numbers of detected remote control(s) are stored (step 404). If there was no previously detected remote control 150, the controller 102 returns to step 402 to continue to monitor for a remote control detected within the predetermined distance to the column head 26. If there was a previously detected remote control 150, the controller 102 sends release information for transfer controls and allows any transfer command (with the optional exception of an emergency transfer command) while also deleting the stored serial number of the previously detected remote control 150 (step 406). The controller 102 then returns to step 402 after a set delay of, for example, 250 ms.

If a remote control 150 is detected within the predetermined distance in step 402, the controller 102 transfers and stores the serial number of the detected remote control via RFID to a table (step 408). Then, the controller 102 sends block information for transfer controls and forbids any transfer command with the optional exception of an emergency transfer command (step 410). Next, the controller 102 may optionally send an information message to the detected remote control(s) 150 to indicate the situation to the user(s)

(step 412). Next, the controller 102 returns to step 402 after a set delay of, for example, 250 ms, to restart the routine.

Figure 7:
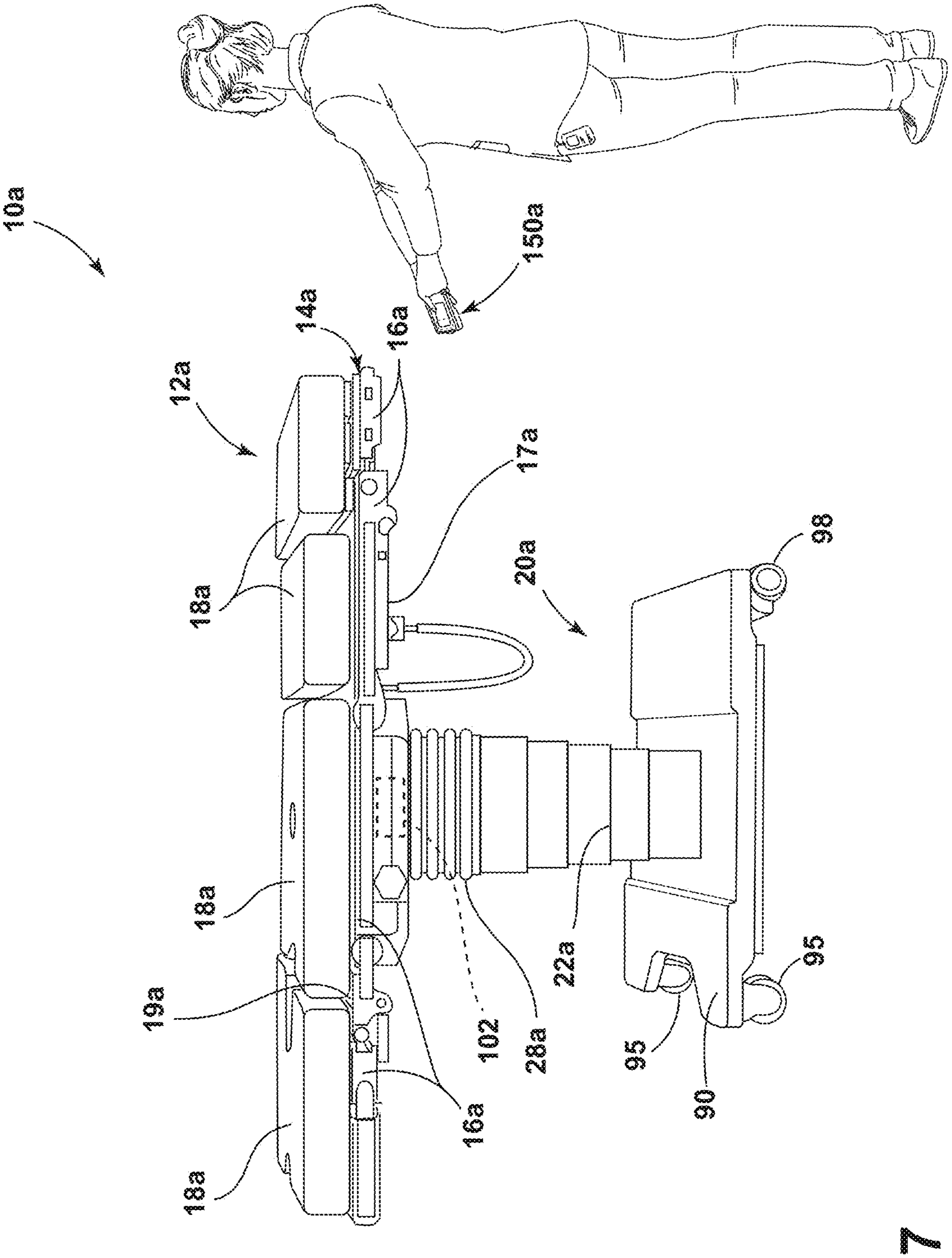
FIG. 7 is an elevational perspective side view of a patient support apparatus according to a second embodiment.

As shown in FIG. 7, a second embodiment of a patient support apparatus 10*a* includes a table 12*a* having a support frame 14*a*, a support structure 20*a* that may optionally include a chassis 90 and a support column 22*a* extending between the chassis 90 and the support frame 14*a*. While the patient support apparatus 10*a* is illustrated with a single support column 22*a*, it is contemplated that other configurations of the support structure 20*a* are contemplated without departing from the teachings herein (e.g., more than one support column 22*a* may extend between the chassis 90 and the support frame 14*a*, etc.). The chassis 90 includes wheels 95 that engage an underlying floor surface. In this way, the patient support apparatus 10 is transportable about the surgical suite or otherwise within a hospital, medical facility, or other healthcare setting. A motor 126 (FIG. 4) may be provided to drive one or more of the wheels 95 under control of the controller 102. Such a motor-driven wheel is often referred to as a fifth wheel. Similar to the table 12 of the first embodiment, the table 12*a* may have segments 16*a*, pads 18*a*, a top surface 19*a* and a bottom surface 17*a*. Unlike the table 12, the table 12*a* may be configured to be fixedly attached to the support structure 20*a* so as to not be removable. Such a movable patient support apparatus is known in the art and part of the TruSystem™ 7000 available from Trumpf Medical or the TS7000 available from Hill-Rom. Additional details of the operation of the TruSystem™ 7000/TS7000 may be found in their respective operating manuals.

Figure 8:
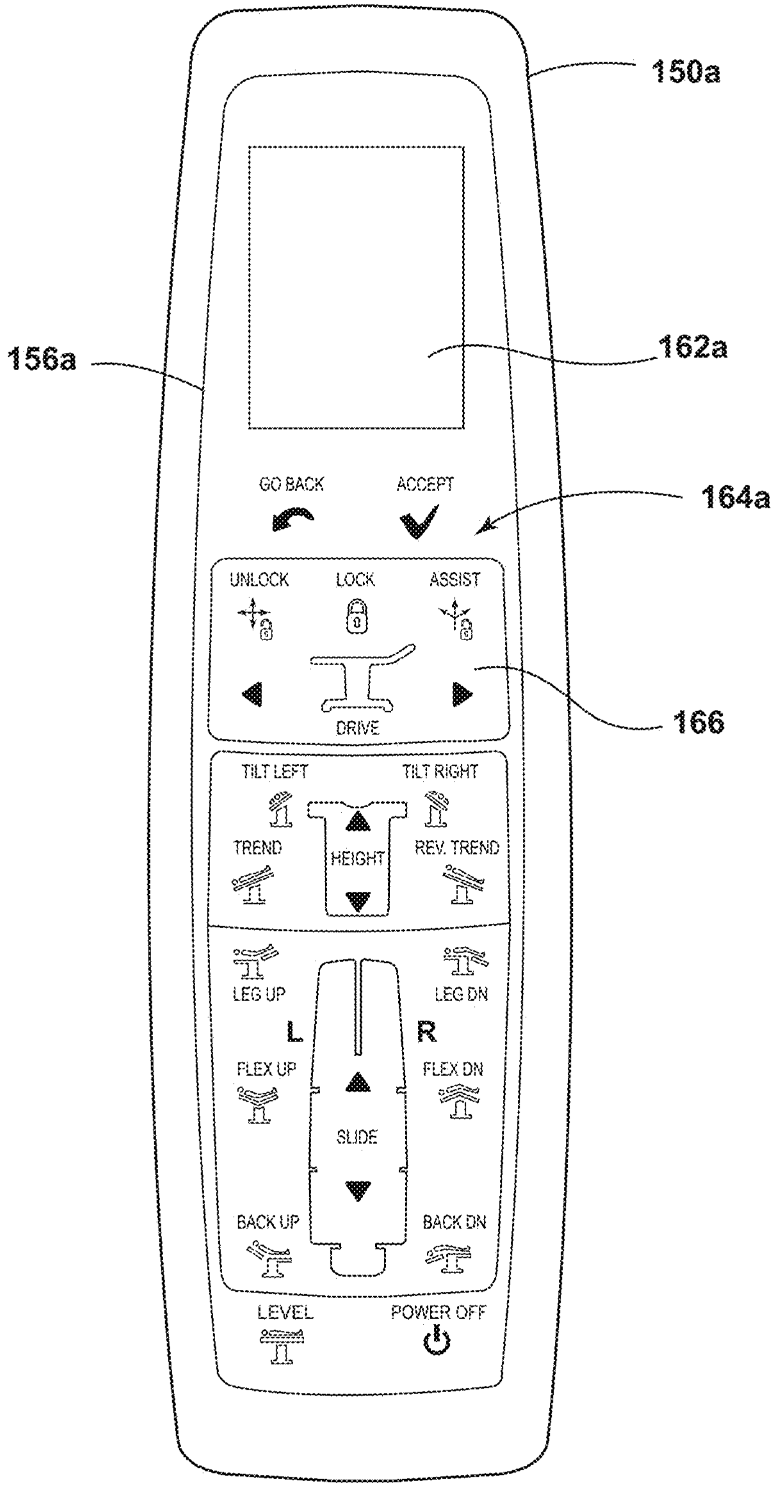
FIG. 8 is a top plan view of a remote control that is used with the patient support apparatus shown in FIG. 7.

FIG. 8 shows a remote control 150*a* for wirelessly controlling the patient support apparatus 10*a*. The circuit components of patient support apparatus 10*a* and remote control 150*a* may be the same as the first embodiment and are also depicted in FIG. 4. Thus, the remote control 150*a* would also include an RFID tag 158. Remote control 150*a* differs from remote control 150 in that it does not include the transfer button 165 and instead includes movement buttons 166 that may be pressed to effect forward or backward movement of the patient support apparatus 10*a*.

A problem with a patient support apparatus 10*a* that is movable with a motor 126 occurs if the remote control 150*a* is located too far away (e.g., more than about 2 m) from the mobile patient support apparatus 10*a* due to safety concerns. To solve this problem, the first RF reader 122 and first RFID tag 158 may be configured such that the RFID tag 158 and hence the remote control 150*a* is not detected if it is at a distance from the patient support apparatus 10*a* of greater than a predetermined distance (e.g., 2 m). Thus, the first RF reader 122, the first RFID tag 158, and appropriately configured controller 102 may serve as a movement prevention means. The controller 102 may be appropriately configured by executing the routine 450 shown in FIG. 9, which is discussed further below. Although the movement prevention means prevents a person from causing the motor 126 to operate and thereby propel the patient support apparatus 10*a*, the movement prevention means does not prevent the controller 102 from performing any other functions in response to the remote control 150*a*.

Figure 9:
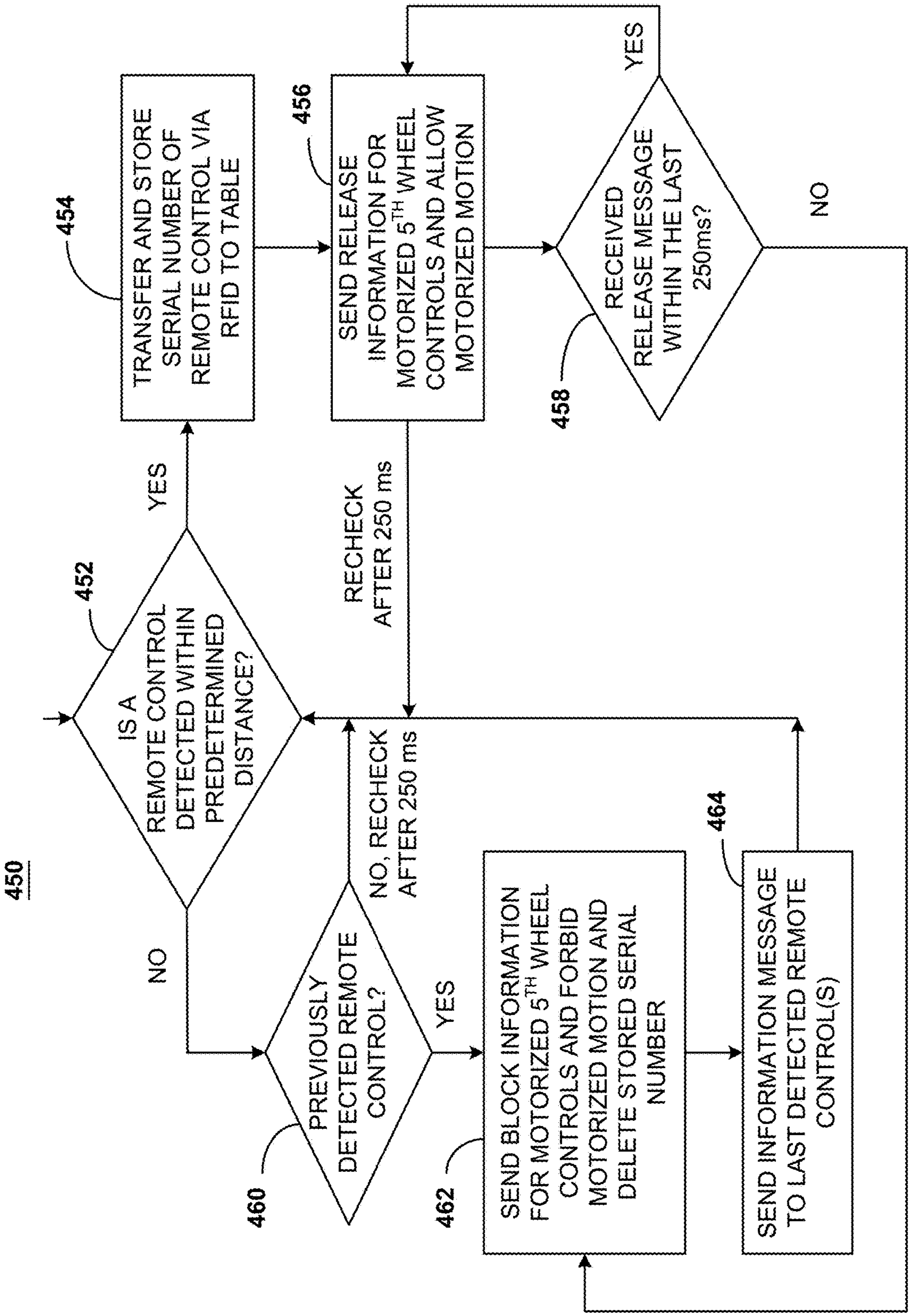
FIG. 9 is a flow chart showing a routine executed by the controller shown in FIG. 4 when used for the patient support apparatus shown in FIG. 7.

FIG. 9 shows a flowchart of a routine 450 executed by the controller 102 to perform the above prevention of the operation of the motor 126 when the remote control 150*a* is too far away from the patient support apparatus 10*a*. The routine 450 beings with the controller 102 determining if a remote control 150*a* is within a predetermined distance (e.g., about 2 m) from the patient support apparatus 10*a* (step 452). As noted above, the RF reader 122/RFID tag 158 has a range corresponding to the predetermined distance such that, when the RF reader 122 senses the RFID tag 158, it informs the controller 102 that the remote control 150*a* is within range (the predetermined distance). If the remote control 150*a* is within the predetermined distance, the controller 102 transfers and stores the serial number of the RFID tag 158 as read by the RF reader 122 to a look-up table (step 454). Then, the controller 102 sends release information for motorized wheel operation and allows the motor 126 to be activated in response to signals from the remote control 150*a* when movement buttons 166 are actuated (step 456). The controller 102 continues to recheck at periodic intervals (e.g., every 250 ms) whether the remote control 150*a* is within the predetermined distance by repeating steps 452-456. A monitoring circuit may monitor for the release signal to be sent during each periodic interval (step 458). So long as a release signal is sent with each passing interval, the controller 102 continues to loop through steps 452-456 while motorized movement is permitted. If, however, a release signal is not sent within the periodic interval, the monitoring circuit will cause the controller 102 to proceed to step 462 whereby movement is blocked as discussed further below.

If the controller 102 determines in step 452 that the remote control 150*a* is not within the predetermined distance, the controller 102 determines if there was a previously detected remote control 150*a* by checking the look-up table (step 460). If no remote control 150*a* was previously detected, the controller 102 rechecks at periodic intervals (e.g., every 250 ms) by looping through steps 452 and 460. If a remote control 150*a* was previously detected, the controller 102 sends block information for motorized fifth wheel controls and prevents motorized movement by preventing actuation of the motor 126 (step 462). The controller 102 also deletes the stored serial number of the previously detected remote control 150*a* from the look-up table (also step 462). The controller 102 may also send an information message to the last detected remote control(s) 150*a* so that if a user attempts to use the remote control 150*a*, a message will appear that informs the user that the remote control 150*a* needs to be brought within the predetermined distance of the patient support apparatus 10*a* to control motion (step 464). The process then returns to step 452 to continue to look for a remote control 150*a* within the predetermined distance. It should be noted that the controller 102 does not otherwise stop responding to any paired remote control(s) to perform other functions. Here it just prevents control of the motorized movement of the patient support apparatus 10*a* using the remote control(s) 150*a* if they are beyond the predetermined distance (e.g., 2 m).

Although the table 12*a* is described above as not being removable from the support structure 20*a*, it is possible to configure the table 12*a* and support structure 20*a* so that table 12*a* is removable in the manner discussed above with respect to the removable table 12 of the first embodiment. In this case, a motorized patient support apparatus would be provided with a removable table, and it would be desirable to provide both the transfer prevention means and the movement prevention means. It may be possible to use the first RF reader and the first RFID tag 158 to detect whether a remote control 150*a* is within a first predetermined distance (e.g., 30 cm) of the column head 26 or within a second predetermined distance (e.g., 2 m) so as to both prevent transfer of the removable table when the remote control 150*a* is too close to the column head 26 and to prevent motorized movement of the patient support apparatus 10*a* when the remote control 150*a* is too far away. Nevertheless, it may be desirable to use a second RFID tag 160 and/or a second RF reader 124 to determine whether the remote control 150*a* is within the second predetermined distance. For example, in a first arrangement, the first RF reader 122 and the first RFID tag 158 may be configured such that the first RF reader 122 only receives a reply signal from the first RFID tag 158 when the remote control 150*a* is within a first predetermined distance (e.g., 30 cm) and the second RF reader 124 and the second RFID tag 160 may be configured such that the second RF reader 124 only receives a reply signal from the second RFID tag 160 when the remote control 150*a* is within a second predetermined distance (e.g., 2 m). Thus, features of the two embodiments may be combined.

Alternatively, only a first RF reader 122 is provided to detect both the first RFID tag 158 and the second RFID tag 160 and where the two RFID tags are configured to transmit signals over different ranges with a first range corresponding to the first predetermined distance and the second range corresponding to the second predetermined distance.

According to yet another alternative, both a first RF reader 122 and a second RF reader 124 are provided that both detect reply signals from a single RFID tag 158 where the two RF readers have different ranges of sensitivity and/or transmission that correspond to the first and second predetermined distances.

The controller 102 may include various types of control circuitry, digital and/or analog, and may include one or more microprocessors, microcontrollers, application-specific integrated circuits (ASIC), or other circuitry configured to perform various input/output, control, analysis, and other functions described herein.

The embodiments disclosed herein are further summarized in the following paragraphs and are further characterized by combinations of any and all of the various aspects described therein.

According to one aspect of the present disclosure, a support structure is provided for supporting a removable table of a patient support apparatus, the support structure comprising: a support column having an adjustable height, the support column including a column head at an upper end of the support column for receiving and supporting the removable table; an actuator for adjusting the height of the support column; a wireless receiver for receiving control signals from a remote control; an RF reader positioned proximate the column head for receiving RF signals from an RFID tag on the remote control; a user interface positioned on the support column for providing control signals; and a controller coupled to the user interface, the actuator, the wireless receiver, and to the RF reader for controlling the actuator in response to control signals, wherein the controller is configured to detect whether the remote control is within a predetermined distance from the column head and to disable upward movement of the support column when the remote control is detected within the predetermined distance.

According to another aspect of the disclosure, the controller detects whether the remote control is within a predetermined distance based on detection of RF signals received by the RF reader from the RFID tag.

According to another aspect of the disclosure, the controller detects whether the remote control is within a predetermined distance based on detection of RF signals received by the RF reader from the RFID tag.

According to another aspect of the disclosure, the predetermined distance is about 30 centimeters.

According to another aspect of the disclosure, the support structure further comprises a base plate for positioning the support structure on a floor of an operating room, where the support column is secured to the base plate.

According to another aspect of the disclosure, the support structure further comprises a chassis and wheels attached to the chassis for moving the support structure, wherein the support column is secured to the chassis.

According to another aspect of the disclosure, the support structure further comprises a motor for selectively driving one of the wheels to provide motorized movement of the patient support apparatus.

According to another aspect of the disclosure, the support structure further comprises a motor for rotating at least one of the plurality of wheels to propel the patient support apparatus in at least one direction, wherein the controller is coupled to the motor, wherein the controller is configured to detect whether the remote control is within a second predetermined distance from the table and wherein the controller is further configured to disable actuation of the motor in response to control signals received from the remote control when the remote control is not detected within the second predetermined distance.

According to another aspect of the disclosure, the second predetermined distance is about 2 meters.

According to another aspect of the disclosure, the controller controls a plurality of functions of the patient support apparatus in response to control signals from the remote control, wherein one of the functions is the actuation of the motor, wherein the controller controls the other functions of the patient support apparatus in response to control signals from the remote control regardless of the detection of the remote control within the second predetermined distance.

According to another aspect of the disclosure, the controller periodically checks whether a remote control is within the predetermined distance.

According to another aspect of the disclosure, the removable table is an operating table having a plurality of movable segments controlled by the controller.

According to another aspect of the present disclosure, a patient support apparatus is provided comprising: a removable table; a support structure comprising a support column having an adjustable height, the support column having a column head at an upper end thereof for receiving and supporting the removable table; an actuator for adjusting the height of the support column; a remote control; a wireless receiver for receiving control signals from the remote control; an RF reader for receiving RF signals from an RFID tag, wherein one of the RF reader and the RFID tag is on the remote control and the other of the RF reader and the RFID tag is positioned proximate the column head; and a controller coupled to the actuator and the wireless receiver, the controller being in communication with the RF reader for controlling the actuator in response to control signals from the remote control, wherein the controller is configured to detect whether the remote control is within a predetermined distance from the column head and to disable upward movement of the support column when the presence of the remote control is detected within the predetermined distance.

According to another aspect of the disclosure, the controller detects whether the remote control is within a predetermined distance based on detection of RF signals received by the RF reader from the RFID tag.

According to another aspect of the disclosure, the predetermined distance is about 30 centimeters.

According to another aspect of the disclosure, the support structure further comprises a base plate for positioning the support structure on a floor of an operating room, where the support column is secured to the base plate.

According to another aspect of the disclosure, the support structure further comprises a chassis and wheels attached to the chassis for moving the support structure, wherein the support column is secured to the chassis.

According to another aspect of the disclosure, the support structure further comprises a motor for selectively driving one of the wheels to provide motorized movement of the patient support apparatus.

According to another aspect of the disclosure, the support structure further comprises a motor for rotating at least one of the plurality of wheels to propel the patient support apparatus in at least one direction, wherein the controller is coupled to the motor, wherein the controller is configured to detect whether the remote control is within a second predetermined distance from the table and wherein the controller is further configured to disable actuation of the motor in response to control signals received from the remote control when the remote control is not detected within the second predetermined distance.

According to another aspect of the disclosure, the second predetermined distance is about 2 meters.

According to another aspect of the disclosure, the controller controls a plurality of functions of the patient support apparatus in response to control signals from the remote control, wherein one of the functions is the actuation of the motor, wherein the controller controls the other functions of the patient support apparatus in response to control signals from the remote control regardless of the detection of the remote control within the second predetermined distance.

According to another aspect of the disclosure, the controller periodically checks whether a remote control is within the predetermined distance.

According to another aspect of the disclosure, the table is an operating table having a plurality of moveable segments controlled by the controller.

According to an aspect of the present disclosure, a patient support apparatus is provided comprising: a support structure comprising: a chassis having a plurality of wheels for allowing movement of the patient support apparatus; a motor for rotating at least one of the plurality of wheels to propel the patient support apparatus in at least one direction; and a support column supported on the chassis; a table supported by the support column; a remote control; a wireless receiver for receiving control signals from the remote control; an RF reader for receiving RF signals from an RFID tag, wherein one of the RF reader and the RFID tag is on the remote control and the other of the RF reader and the RFID tag is associated with the support structure; and a controller coupled to the motor and the wireless receiver, the controller being in communication with the RF reader for controlling a plurality of functions of the patient support apparatus in response to control signals from the remote control, wherein one of the functions is the actuation of the motor, wherein the controller is configured to detect whether the remote control is within a predetermined distance from the table and wherein the controller is further configured to disable actuation of the motor in response to control signals received from the remote control when the presence of the remote control is not detected within the predetermined distance, wherein the controller controls the other functions of the patient support apparatus in response to control signals from the remote control regardless of the detection of the remote control within the predetermined distance.

According to another aspect of the disclosure, the predetermined distance is about 2 meters.

According to another aspect of the disclosure, the controller periodically checks whether a remote control is within the predetermined distance.

According to another aspect of the disclosure, the controller detects whether the remote control is within a predetermined distance based on detection of RF signals received by the RF reader from the RFID tag.

According to another aspect of the disclosure, the table is a removable table.

According to another aspect of the disclosure, the patient support apparatus further comprises: an actuator for adjusting a height of the support column, wherein the support column has a column head at an upper end thereof for receiving and supporting the removable table, wherein the RF reader is positioned proximate the column head, and wherein the controller is coupled to the actuator for controlling the actuator in response to control signals from the remote control, wherein the controller is configured to detect whether the remote control is within a second predetermined distance from the column head and to disable upward movement of the support column when the remote control is detected within the second predetermined distance.

According to another aspect of the disclosure, the second predetermined distance is about 30 centimeters.

According to another aspect of the disclosure, the controller periodically checks whether a remote control is within the second predetermined distance.

According to another aspect of the disclosure, the patient support apparatus further comprises: an actuator for adjusting a height of the support column, wherein the support column has a column head at an upper end thereof for receiving and supporting the removable table; and a second RF reader positioned proximate the column head for receiving RF signals from the RFID tag on the remote control, wherein the controller is coupled to the second RF reader and the actuator for controlling the actuator in response to control signals from the remote control, wherein the controller is configured to detect whether the remote control is within a second predetermined distance from the column head and to disable upward movement of the support column when the remote control is detected within the second predetermined distance.

According to another aspect of the disclosure, the controller detects whether the remote control is within the second predetermined distance based on detection of RF signals received by the second RF reader from the RFID tag.

According to another aspect of the disclosure, the patient support apparatus further comprises: an actuator for adjusting a height of the support column, wherein the support column has a column head at an upper end thereof for receiving and supporting the removable table; and a second RF reader positioned proximate the column head for receiving RF signals from a second RFID tag on the remote control, wherein the controller is coupled to the second RF reader and the actuator for controlling the actuator in response to control signals from the remote control, wherein the controller is configured to detect whether the remote control is within a second predetermined distance from the column head and to disable upward movement of the support column when the remote control is detected within the second predetermined distance.

According to another aspect of the disclosure, the controller detects whether the remote control is within the second predetermined distance based on detection of RF signals received by the second RF reader from the second RFID tag.

According to another aspect of the disclosure, the table is an operating table having a plurality of moveable segments controlled by the controller.

According to one aspect of the present disclosure, a method is provided of controlling a transfer of a removable operating table from a shuttle to a support structure having a support column having an adjustable height, the support column having a column head at an upper end thereof for receiving and supporting the removable operating table, the method comprising the steps of: detecting whether a remote control is within a predetermined distance from the column head; disabling upward movement of the support column when the remote control is detected within the predetermined distance; and allowing upward movement of the support column when the remote control is not detected within the predetermined distance, wherein such upward movement of the support column lifts the operating table upward off the shuttle to transfer the operating table from the shuttle to the support structure.

According to another aspect of the disclosure, the method further comprises the steps of: providing a wireless receiver for receiving control signals from a remote control; providing an RFID tag on the remote control; and providing an RF reader positioned proximate the column head for receiving RF signals from the RFID tag on the remote control, wherein the step of detecting whether a remote control is within a predetermined distance from the column head is based on detection of RF signals received by the RF reader from the RFID tag.

According to another aspect of the disclosure, the method further comprises the step of providing an actuator for adjusting the height of the support column, wherein the step of disabling upward movement of the support column includes disabling operation of the actuator.

According to another aspect of the disclosure, the predetermined distance is about 30 centimeters.

According to an aspect of the present disclosure, a patient support apparatus comprises: a removable table; a support structure comprising a support column having an adjustable height, the support column having a column head at an upper end thereof for receiving and supporting the removable table; an actuator for adjusting the height of the support column and performing a transfer function by raising the column head to engage the removable table; a wireless receiver for receiving control signals from a remote control; detection means for detecting a remote control within a predetermined distance of the column head; and transfer prevention means for preventing a transfer function to be performed when the detection means detects a remote control within the predetermined distance of the column head.

According to another aspect of the disclosure, the detection means comprises an RF reader for receiving RF signals from an RFID tag on the remote control; and a controller coupled to the RF reader, wherein the controller is configured to detect whether the remote control is within a predetermined distance from the column head based on detection of RF signals received by the RF reader from the RFID tag.

According to another aspect of the disclosure, the transfer prevention means comprises the controller configured to control the actuator and to prevent the actuator from raising the column head when the remote control is detected within the predetermined distance from the column head.

According to another aspect of the disclosure, the transfer prevention means comprises a controller configured to control the actuator and to prevent the actuator from raising the column head when a remote control is detected within the predetermined distance from the column head.

According to an aspect of the present disclosure, a patient support apparatus comprises: a support structure comprising: a chassis having a plurality of wheels for allowing movement of the patient support apparatus; a motor for rotating at least one of the plurality of wheels to propel the patient support apparatus in at least one direction; and a support column supported on the chassis. The patient support apparatus further comprises a table supported by the support column; a wireless receiver for receiving control signals from a remote control; detection means for detecting a remote control within a predetermined distance of the column head; and movement prevention means for preventing operation of the motor in response to control signals received from the remote control when the detection means does not detect a remote control within the predetermined distance, wherein other adjustment functions of the patient support apparatus are performed in response to a signal from a remote control regardless of whether the remote control is detected within the predetermined distance.

According to another aspect of the disclosure, the detection means comprises an RF reader for receiving RF signals from an RFID tag on the remote control; and a controller coupled to the RF reader, wherein the controller is configured to detect whether the remote control is within a predetermined distance based on detection of RF signals received by the RF reader from the RFID tag.

According to another aspect of the disclosure, the movement prevention means comprises the controller configured to control the motor and to prevent the motor from operating when the remote control is not detected within the predetermined distance.

According to another aspect of the disclosure, the movement prevention means comprises a controller configured to control the motor and to prevent the motor from operating when the remote control is not detected within the predetermined distance.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term “coupled” (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A support structure for supporting a removable table of a patient support apparatus, the support structure comprising:
- a support column having an adjustable height, the support column including a column head at an upper end of the support column for receiving and supporting the removable table;
- an actuator for adjusting the height of the support column;
- a wireless receiver for receiving remote control signals from a remote control;
- an RF reader positioned proximate the column head for receiving RF signals from an RFID tag on the remote control;
- a user interface positioned on the support column for providing control signals; and
- a controller coupled to the user interface, the actuator, the wireless receiver, and to the RF reader for controlling the actuator in response to one of the control signals and the remote control signals, wherein the controller is configured to detect whether the remote control is within a predetermined distance from the column head and to disable upward movement of the support column when the remote control is detected within the predetermined distance.

2. The support structure of claim 1, wherein the controller detects whether the remote control is within a predetermined distance based on detection of RF signals received by the RF reader from the RFID tag.

3. The support structure of claim 1, wherein the predetermined distance is about 30 centimeters.

4. The support structure of claim 1 and further comprising a base plate for positioning the support structure on a floor of an operating room, where the support column is secured to the base plate.

5. The support structure of claim 1 and further comprising a chassis and wheels attached to the chassis for moving the support structure, wherein the support column is secured to the chassis.

6. The support structure of claim 5, wherein the support structure further comprises a motor for selectively driving one of the wheels to provide motorized movement of the patient support apparatus.

7. The support structure of claim 6, wherein the motor rotates at least one of the plurality of wheels to propel the patient support apparatus in at least one direction, wherein the controller is coupled to the motor, wherein the controller is configured to detect whether the remote control is within a second predetermined distance from the table and wherein the controller is further configured to disable actuation of the motor in response to the remote control signals received from the remote control when the remote control is not detected within the second predetermined distance.

8. The support structure of claim 7, wherein the second predetermined distance is about 2 meters.

9. The support structure of claim 7, wherein the controller controls a plurality of functions of the patient support apparatus in response to the remote control signals from the remote control, wherein one of the functions is the actuation of the motor, wherein the controller controls the other functions of the patient support apparatus in response to the remote control signals from the remote control regardless of the detection of the remote control within the second predetermined distance.

10. The support structure of claim 1, wherein the controller periodically checks whether a remote control is within the predetermined distance.

11. The support structure of claim 1, wherein the removable table is an operating table having a plurality of movable segments controlled by the controller.

12. A patient support apparatus comprising the removable table and the support structure of claim 1.

13. A patient support apparatus comprising:
- a removable table;
- a support structure comprising a support column having an adjustable height, the support column having a column head at an upper end thereof for receiving and supporting the removable table;
- an actuator for adjusting the height of the support column;
- a remote control;
- a wireless receiver for receiving control signals from the remote control;
- an RF reader for receiving RF signals from an RFID tag, wherein one of the RF reader and the RFID tag is on the remote control and the other of the RF reader and the RFID tag is positioned proximate the column head; and
- a controller coupled to the actuator and the wireless receiver, the controller being in communication with the RF reader for controlling the actuator in response to the control signals from the remote control, wherein the controller is configured to detect whether the remote control is within a predetermined distance from the column head and to disable upward movement of the support column when the presence of the remote control is detected within the predetermined distance.

14. The patient support apparatus of claim 13, wherein the controller detects whether the remote control is within a predetermined distance based on detection of RF signals received by the RF reader from the RFID tag.

15. The patient support apparatus of claim 13, wherein the predetermined distance is about 30 centimeters.

16. The patient support apparatus of claim 13, wherein the support structure further comprises a base plate for positioning the support structure on a floor of an operating room, where the support column is secured to the base plate.

17. The patient support apparatus of claim 13, wherein the support structure further comprises a chassis and wheels attached to the chassis for moving the support structure, wherein the support column is secured to the chassis.

18. The patient support apparatus of claim 17, wherein the support structure further comprises a motor for selectively driving one of the wheels to provide motorized movement of the patient support apparatus.

19. The patient support apparatus of claim 18, wherein the support structure further comprises a motor for rotating at least one of the plurality of wheels to propel the patient support apparatus in at least one direction, wherein the controller is coupled to the motor, wherein the controller is configured to detect whether the remote control is within a second predetermined distance from the table and wherein the controller is further configured to disable actuation of the motor in response to the control signals received from the remote control when the remote control is not detected within the second predetermined distance.

20. The patient support apparatus of claim 19, wherein the second predetermined distance is about 2 meters.

21. The patient support apparatus of claim 19, wherein the controller controls a plurality of functions of the patient support apparatus in response to the control signals from the remote control, wherein one of the functions is the actuation of the motor, wherein the controller controls the other functions of the patient support apparatus in response to control signals from the remote control regardless of the detection of the remote control within the second predetermined distance.

22. The patient support apparatus of claim 13, wherein the controller periodically checks whether a remote control is within the predetermined distance.

23. The patient support apparatus of claim 13, wherein the removable table is an operating table having a plurality of movable segments controlled by the controller.

24. A patient support apparatus comprising:

- a support structure comprising:
  - a chassis having a plurality of wheels for allowing movement of the patient support apparatus;
  - a motor for rotating at least one of the plurality of wheels to propel the patient support apparatus in at least one direction; and
  - a support column supported on the chassis;
- a table supported by the support column;
- a remote control;
- a wireless receiver for receiving control signals from the remote control;
- an RF reader for receiving RF signals from an RFID tag, wherein one of the RF reader and the RFID tag is on the remote control and the other of the RF reader and the RFID tag is associated with the support structure; and
- a controller coupled to the motor and the wireless receiver, the controller being in communication with the RF reader for controlling a plurality of functions of the patient support apparatus in response to control signals from the remote control, wherein one of the plurality of functions is the actuation of the motor, wherein the controller is configured to detect whether the remote control is within a predetermined distance from the table and wherein the controller is further configured to disable actuation of the motor in response to the control signals received from the remote control when the remote control is not detected within the predetermined distance, wherein the controller controls the other of plurality of functions of the patient support apparatus in response to the control signals from the remote control regardless of the detection of the remote control within the predetermined distance.

25. The patient support apparatus of claim 24, wherein the predetermined distance is about 2 meters.

26. The patient support apparatus of claim 24, wherein the controller periodically checks whether a remote control is within the predetermined distance.

27. The patient support apparatus of claim 24, wherein the controller detects whether the remote control is within a predetermined distance based on detection of RF signals received by the RF reader from the RFID tag.

28. The patient support apparatus of claim 24, wherein the table is a removable table.

29. The patient support apparatus of claim 28 and further comprising:

- an actuator for adjusting a height of the support column, wherein the support column has a column head at an upper end thereof for receiving and supporting the removable table,
- wherein the RF reader is positioned proximate the column head, and
- wherein the controller is coupled to the actuator for controlling the actuator in response to the control signals from the remote control, wherein the controller is configured to detect whether the remote control is within a second predetermined distance from the column head and to disable upward movement of the support column when the remote control is detected within the second predetermined distance.

30. The patient support apparatus of claim 29, wherein the second predetermined distance is about 30 centimeters.

31. The patient support apparatus of claim 29, wherein the controller periodically checks whether a remote control is within the second predetermined distance.

32. The patient support apparatus of claim 28 and further comprising:

- an actuator for adjusting a height of the support column, wherein the support column has a column head at an upper end thereof for receiving and supporting the removable table; and
- a second RF reader positioned proximate the column head for receiving RF signals from the RFID tag on the remote control,
- wherein the controller is coupled to the second RF reader and the actuator for controlling the actuator in response to the control signals from the remote control, wherein the controller is configured to detect whether the remote control is within a second predetermined distance from the column head and to disable upward movement of the support column when the remote control is detected within the second predetermined distance.

33. The patient support apparatus of claim 32, wherein the controller detects whether the remote control is within the second predetermined distance based on detection of RF signals received by the second RF reader from the RFID tag.

34. The patient support apparatus of claim 28 and further comprising:

- an actuator for adjusting a height of the support column, wherein the support column has a column head at an upper end thereof for receiving and supporting the removable table; and
- a second RF reader positioned proximate the column head for receiving RF signals from a second RFID tag on the remote control,
- wherein the controller is coupled to the second RF reader and the actuator for controlling the actuator in response to the control signals from the remote control, wherein the controller is configured to detect whether the remote control is within a second predetermined distance from the column head and to disable upward movement of the support column when the remote control is detected within the second predetermined distance.

35. The patient support apparatus of claim 34, wherein the controller detects whether the remote control is within the second predetermined distance based on detection of RF signals received by the second RF reader from the second RFID tag.

36. The patient support apparatus of claim 24, wherein the table is an operating table having a plurality of moveable segments controlled by the controller.

37. A method of controlling a transfer of a removable operating table from a shuttle to a support structure having a support column having an adjustable height, the support column having a column head at an upper end thereof for receiving and supporting the removable operating table, the method comprising the steps of:

detecting whether a remote control is within a predetermined distance from the column head;

disabling upward movement of the support column when the remote control is detected within the predetermined distance; and allowing upward movement of the support column when the remote control is not detected within the predetermined distance, wherein such upward movement of the support column lifts the operating table upward off the shuttle to transfer the operating table from the shuttle to the support structure.

38. The method of claim 37 and further comprising the steps of:

providing a wireless receiver for receiving control signals from a remote control;

providing an RFID tag on the remote control; and providing an RF reader positioned proximate the column head for receiving RF signals from the RFID tag on the remote control, wherein the step of detecting whether a remote control is within a predetermined distance from the column head is based on detection of RF signals received by the RF reader from the RFID tag.

39. The method of claim 37 and further comprising the step of providing an actuator for adjusting the height of the support column, wherein the step of disabling upward movement of the support column includes disabling operation of the actuator.

40. The method of claim 37, wherein the predetermined distance is about 30 centimeters.

* * * * *